United States Patent [19]
Russell et al.

[11] Patent Number: 5,971,998
[45] Date of Patent: Oct. 26, 1999

[54] SUPPORT DEVICE AND METHOD FOR CONTROLLING BREAST THICKNESS DURING STEREOTACTIC GUIDED NEEDLE BIOPSY

[75] Inventors: Donald G. Russell, 86 Windsor Rd., Kensington, Conn. 06037; Stewart E. Bober, 3 Pheasant Chase, West Hartford, Conn. 06117

[73] Assignees: Donald G. Russell, Kensington; Stewart E. Bober, West Hartford, both of Conn.

[21] Appl. No.: 09/052,659

[22] Filed: Mar. 31, 1998

[51] Int. Cl.⁶ .................................................... A61B 19/00

[52] U.S. Cl. ............................... 606/130; 606/1; 606/97; 378/37; 378/208; 604/369

[58] Field of Search .................................. 606/130, 1, 97; 604/369; 600/231, 227; 5/630, 397, 398, 400; 378/37, 208

[56] References Cited

U.S. PATENT DOCUMENTS

| | | | |
|---|---|---|---|
| 4,691,333 | 9/1987 | Gabriele et al. | 378/37 |
| 5,507,049 | 4/1996 | Lane | 5/484 |

*Primary Examiner*—Michael Buiz
*Assistant Examiner*—Lien Nao
*Attorney, Agent, or Firm*—Cummings & Lockwood

[57] ABSTRACT

A support device for controlling breast thickness during stereotactic guided needle biopsy is provided. The support device includes a compressible support having an inner surface which extends adjacent to a substantial portion of a peripheral surface of a patient's breast when the breast and the support are disposed between the fixed and pressure plates of an apparatus for performing stereotactic guided needle biopsy. The compressible support restricts the inferior and lateral excursion of the breast as the plates are moved toward one another and the patient's breast and the compressible support are pressed between the plates. A method for controlling breast thickness during stereotactic guided needle biopsy is also provided.

20 Claims, 3 Drawing Sheets

SUPPORT DEVICE AND METHOD FOR CONTROLLING BREAST THICKNESS DURING STEREOTACTIC GUIDED NEEDLE BIOPSY

FIELD OF THE INVENTION

This invention concerns a device and a method for controlling the thickness of a patient's breast during the procedure of stereotactic guided needle breast biopsy. More particularly, this invention concerns a support device that is positioned adjacent to a patient's breast to limit the inferior and lateral excursion of the breast tissue as the breast is pressed during needle biopsy, which results in a significant increase in breast thickness.

BACKGROUND OF THE INVENTION

Breast cancer is a leading killer of American women. However, very significant technical improvements in the sensitivity of mammography have been made over the past decade leading to much earlier detection of cancers in many patients. Early diagnosis and treatment results in dramatically improved cure rates. With the improved radiographic resolution which is available in current mammographic studies, radiologists are detecting a greater number of suspicious densities, microcalcifications and other tissue distortions that may represent an early cancer. Biopsy of these suspicious findings is very frequently recommended to determine whether or not the patient has a malignancy.

Customary surgical biopsy is an invasive procedure that requires hospitalization, general anesthesia, a surgical incision and the removal of one or more moderately large tissue specimens to be certain that the area in question is removed. Within the last 5 years, a method of tissue sampling has been developed, wherein a needle or canula is "fired" or injected into and through a suspicious lesion by a spring loaded biopsy device or "gun". In this method, known as stereotactic guided needle biopsy, the sampling needle is guided by preliminary stereotactic radiographs from which the exact location and depth of the lesion is calculated. This information is programmed into the biopsy device so that the sampling needle can be guided to and traverse the area to be sampled. Accuracy of needle placement is plus or minus 2 to 5 mm.

As mentioned above, the sampling needle must pass through the suspicious lesion. The minimum needle "throw" or excursion to obtain a satisfactory core from the lesion is about two centimeters. Since the minimum depth of a lesion to be biopsied in this procedure must be at least 1.0 to 1.5 cm, the actual needle movement is at least 3.5 cm through tissue. For this reason, the breast cannot be reduced in thickness to less than 3.5 cm in order to perform the biopsy by this method.

Newer needles for use in stereotactic guided needle biopsy have a trough about 2.0 cm in length near the tip. When the needle is inserted into a lesion, tissue from the lesion is drawn by suction into the trough and then excised by an inner coring sleeve. Needles of this design are rapidly gaining favor since they provide larger tissue samples which provides more accurate tissue analysis. However, these newer needles must also traverse the length of the tissue to be sampled, and the required amount of breast tissue traversed remains at no less than 3.5 cm.

Known apparatus for performing stereotactic guided needle biopsy is illustrated schematically in FIGS. 1 and 2. The apparatus, generally designated 10, includes a table 12 which can be elevated. The patient lies face down on a mattress 14 supported on the table. and the patient's breast 16 containing a lesion to be biopsied, such as the lesion 17, is suspended through a circular opening 18 approximately 20 cm. in diameter. A fixed, rigid plate 20 is position at one end of the opening 18 adjacent one side of the breast 16. A radiographic recording mechanism 22, either mammography film or an electronic digital recording screen, is located behind the fixed plate. On the other side of the breast, there is a movable, mechanically driven, translucent pressure plate 24 with a window opening 26. A biopsy needle 28, which is mounted in a spring loaded "gun" or injector 29, is aligned with the window opening 26, and a mammography xray tube 30 is positioned proximal to the compression plate.

In practice, the pressure plate is moved toward the fixed plate in the direction indicated by arrow A to moderately press or squeeze the breast between the plates 20 and 24. After initial radiographic images are taken to identify the lesion 17, the window 26 is positioned directly over the lesion. Two stereotactic views are then obtained by angling the xray tube 15 degrees to either side of a central line aimed at the lesion. The figures are programmed into the apparatus to determine the depth of the lesion within the breast.

Under sterile conditions and with local skin anesthesia, the biopsy needle 28 is then inserted into the breast just proximal to the target lesion 17. Accuracy of the needle placement is then assessed by means of another pair of stereo images. If the operator confirms that the area to be biopsied is directly opposite the needle tip, the spring loaded injector then "fires" or injects the needle at a high speed for a distance of about two centimeters so that the needle traverses the length of the lesion. A third set of stereotactic views is then taken. If the needle placement is satisfactory, sampling then proceeds.

As a woman ages, the supportive fibers of the breast lose their elasticity and the fibers elongate. These changes also occur in the skin envelope encompassing the breast. Although there are variations from patient to patient, some breasts become elongated, flaccid, and pendulous. When such a breast is initially pressed between the plates 20 and 24 during the first steps of a stereotactic needle biopsy, the total thickness of the breast can be as little as two centimeters. If the needle is injected in such a case, the 2 cm excursion of the needle will very likely cause the needle to pass through the back side of the breast, impinge on the fixed plate 20, break or penetrate the plate and impale the patient's breast. Accordingly, in cases where the patient's breast, after it is pressed between the plates 20 and 24, is too thin for stereotactic biopsy, i.e., the breast does not have a thickness greater than about 3.5 cm, stereotactic needle biopsy must be abandoned and the biopsy performed with a full surgical approach.

Human tissue is not compressible, i.e., there is no reduction in volume when human tissue and, more particularly, breast tissue is pressed or squeezed. Moreover, the skin has a very limited ability to stretch. Accordingly, when a breast is pressed or squeezed there is no change in the total volume of breast tissue. Instead, the tissue is displaced, flattened and altered in shape up to the limits permitted by the supportive fibers of the breast and the confines of the skin envelope.

When the patient's breast is pressed between the fixed plate 20 and the pressure plate 24 as shown in FIG. 2, the breast generally has the configuration of a half cylinder. The volume, V, of the tissue may be roughly computed by the following mathematical formula:

$$V = \frac{(\pi)(r^2)(h)}{2}$$

Where π is 3.14, r is the radius of the tissue cylinder, and h is the height or thickness of the cylinder.

If the radius r of the patient's breast is reduced, which is accomplished by reducing the area of the breast in contact with the pressure plate, then h or the thickness of the breast must increase in order to reflect the same volume of tissue. This reduction in the breast area in contact with the compression plate may be accomplished by restricting the displacement of the breast interiorly, medially and laterally as it is compressed.

SUMMARY OF THE INVENTION

The present invention provides a support device for controlling the thickness of a patient's breast during stereotactic guided needle biopsy. The device taught by the invention is used in conjunction with an apparatus for performing stereotactic guided needle biopsy of the type having a fixed plate and a pressure plate movable with respect to one another. The device comprises a compressible support having an inner surface which extends adjacent to a substantial portion of a peripheral surface of a patient's breast when the breast and the support are disposed between the fixed plate and the pressure plate of the above-described apparatus. The support controls the thickness of the patient's breast by restricting the inferior and lateral excursion of the breast as the breast and the compressible support are pressed between the plates.

This results in a redistribution of breast tissue characterized by a reduction in the radius of the breast and the surface area of the breast in contact with the plates and a corresponding increase in breast tissue thickness, in accordance with the formula set forth above. Thus, even in patients who would otherwise present a breast thickness of as little as 2 cm when the breast is pressed between the plates, use of the support device results in a redistribution of tissue which provides a breast thickness of at least about 3.5 cm. Accordingly, stereotactic guided needle biopsy can be performed on these patients with a safe, adequate layer of tissue beyond the tip of the injected needle.

In a preferred embodiment, the compressible support is sufficiently resilient so that when the plates are again moved apart to release the pressure on the patient's breast the support assumes it original shape. In a further preferred embodiment, the support device includes a layer of absorbent material disposed between the inner surface of the compressible support and the patient's breast. The layer of absorbent material absorbs and contains blood and other body fluids that may exude from the puncture site of the biopsy needle. In the most preferred embodiment of the invention, the compressible support comprises a flexible foam strip having an inner surface extending adjacent to a substantial portion of a peripheral surface of a patient's breast, and a layer of absorbent material affixed to the inner surface of the foam strip.

A method for controlling the thickness of a patient's breast during stereotactic needle biopsy is also provided.

DETAILED DESCRIPTION OF THE PREFERRED EMBODIMENT

Figure 3:
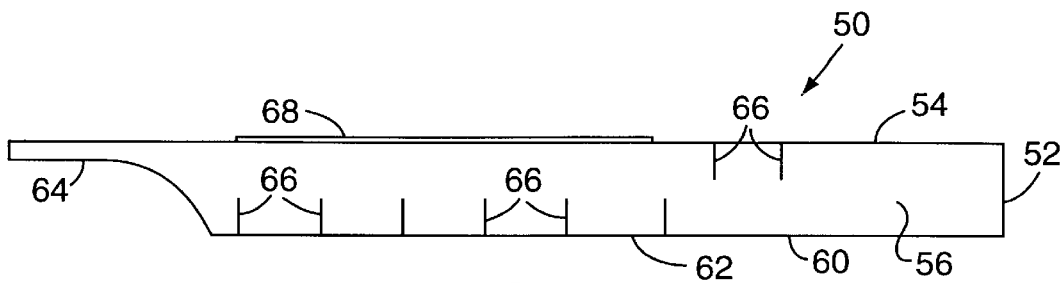
FIG. 3 is a side view of a support device embodying the present invention.
Figure 4:
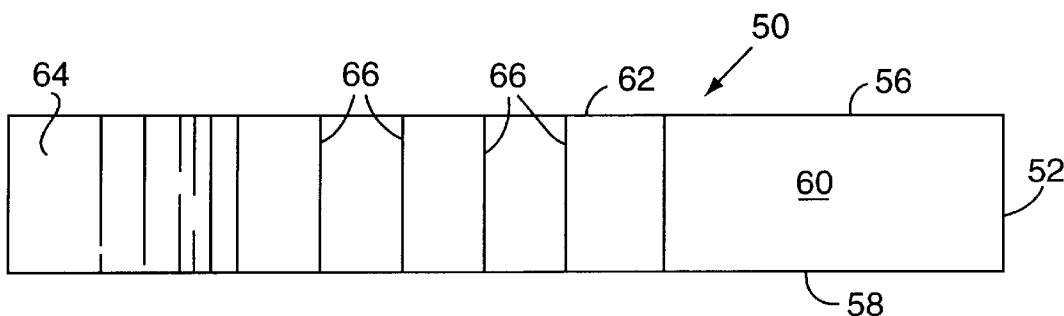
FIG. 4 is a bottom view of the support device shown in FIG. 3.
Figure 5:
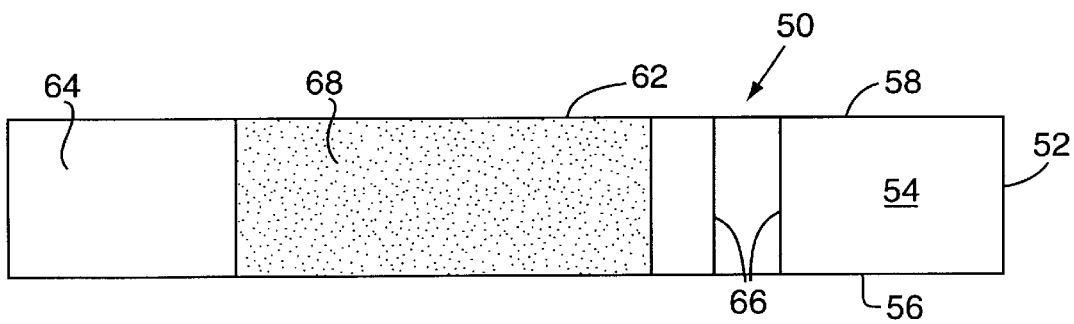
FIG. 5 is a top view of the support device shown in FIG. 3.

FIGS. 3–5 illustrate a support device embodying the present invention. The support device, generally designated 50, comprises a compressible support or bolster 52 having a top surface 54, two side surfaces 56, 58 (one shown in FIG. 3), and a bottom surface 60. The bolster includes a main support portion 62 and an integrally formed tab portion 64 and is defined by a strip of compressible plastic foam. In the illustrated embodiment, the bolter 52 is formed from a strip of open cell urethane foam.

The overall length of the bolster 52 is variable but is satisfactory for all applications at 18 in. (45 cm), with the tab portion 64 having a length about 6 in. (15 cm). If a bolster of reduced length is required for a particular application, the length may be reduced by simply cutting the strip at any convenient point. The height is approximately 2 in. (5 cm), and the support portion 62 of the bolster has a width of approximately 3 in (7.5 cm). The tab portion 64 has a width of about ⅜ in. (4 mm). A plurality of transverse slits 66, 66 are incised across the top and bottom surfaces of the bolster to a depth of 1 or 2 cm to enhance the flexibility of the foam strip, although it should be understood that this is not necessary in all applications.

As illustrated best in FIG. 5, a layer 68 of absorbent material is supported on the top surface 54 of the bolster. As explained further below, the layer 68 of absorbent material contains and absorbs blood and other body fluids exuded from the needle puncture site, thus preventing these fluids from contaminating or even damaging the apparatus 10. The absorbent material comprising the layer 68 may be any sterile absorbent material commonly used in art, and the particular material employed in the illustrated embodiment is non woven methyl cellulose material. The layer 68 of absorbent material may be loosely placed on the top surface 54 of the bolster, or it may be affixed to this surface by, for example, applying adhesive to the bolster or the surface of the layer in contact with the bolster. Since the bolster 52 is intended to be a single use, disposable item, it is preferable to affix the layer 68 to the bolster with adhesive so that both items may be disposed of as a single package.

Figure 6:
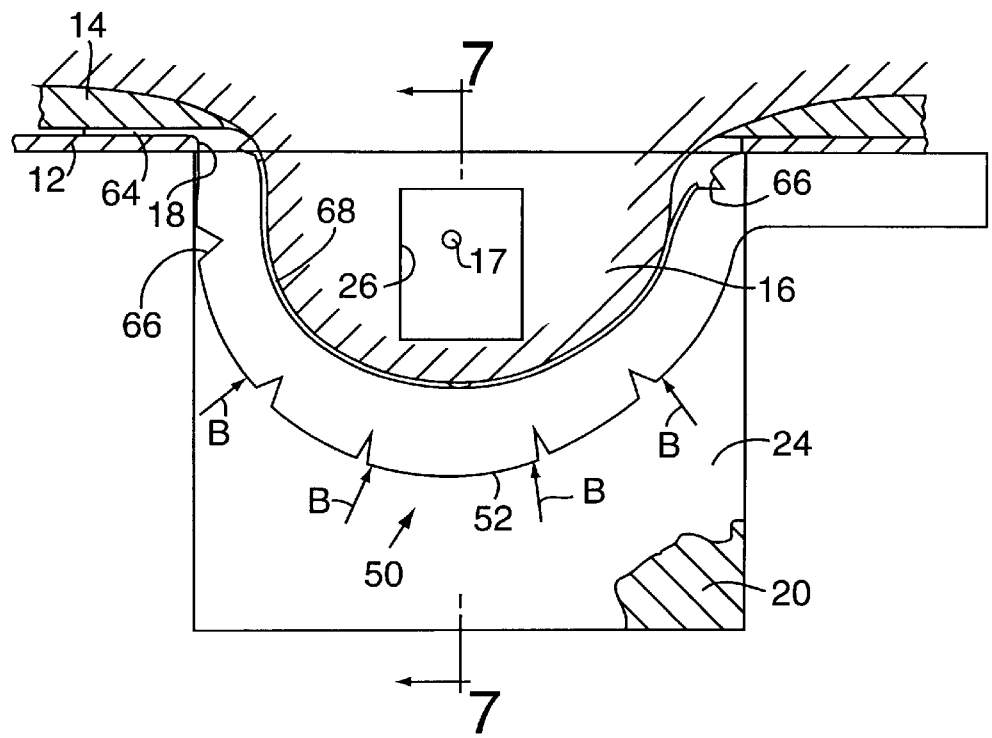
FIG. 6 is a front view of the apparatus shown in FIG. 1 with the patient's breast and the support device of FIG. 3 disposed between the fixed plate and the pressure plate of the apparatus.
Figure 7:
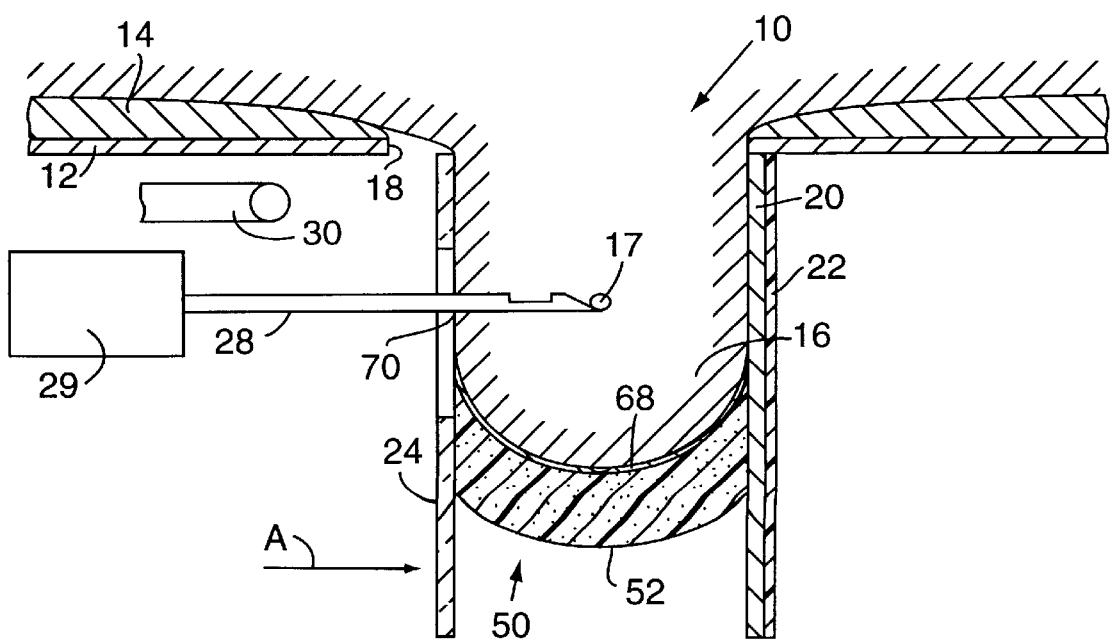
FIG. 7 is a cross section taken along the line 7—7 of the apparatus shown in FIG. 1 with the patient's breast and the support device of FIG. 3 shown pressed between the fixed plate and the pressure plate of the apparatus.

Referring now to FIGS. 6 and 7 the method of using the bolster 52 in a stereotactic guided needle biopsy procedure will be explained. The patient is placed prone or face down on the mattress 14 supported on the table 12, and the patient's breast 16 including the lesion 17 to be biopsied is introduced downwardly through the circular opening 18 formed in the table. As shown in FIG. 6, one end of the bolster 52 is secured to the table 10 by inserting the tab portion 64 between the mattress and the table. The bolster is then swung under the patient's breast and the pressure plate 24 is slowly advanced toward the fixed plate 20 in the direction indicated by arrow A. The foam comprising the bolster 52 compresses as the pressure plate 24 is moved toward the fixed plate 20. Accordingly, the bolster does not in any way hinder or prevent movement of the pressure plate, and once the bolster is pressed between the plates, it is securely but movably held in position between the plates by friction.

While slowly advancing the pressure plate toward the fixed plate, the operator presses upwardly and inwardly on the bolster in the direction indicated by arrows B, B. The bolster is thus manipulated into a cup-like receptacle that extends adjacent to a substantial peripheral portion of the patient's breast, as shown in FIG. 6. As the operator continues to move the pressure plate 24 toward the fixed plate 20 and the patient's breast and the bolster are pressed between the plates, the bolster presses inwardly and upwardly on the patient's breast to restrict the inferior and lateral excursion of the breast. This procedure is continued until the bolster and the patient's breast are in the configuration shown in FIG. 7.

Figure 1:
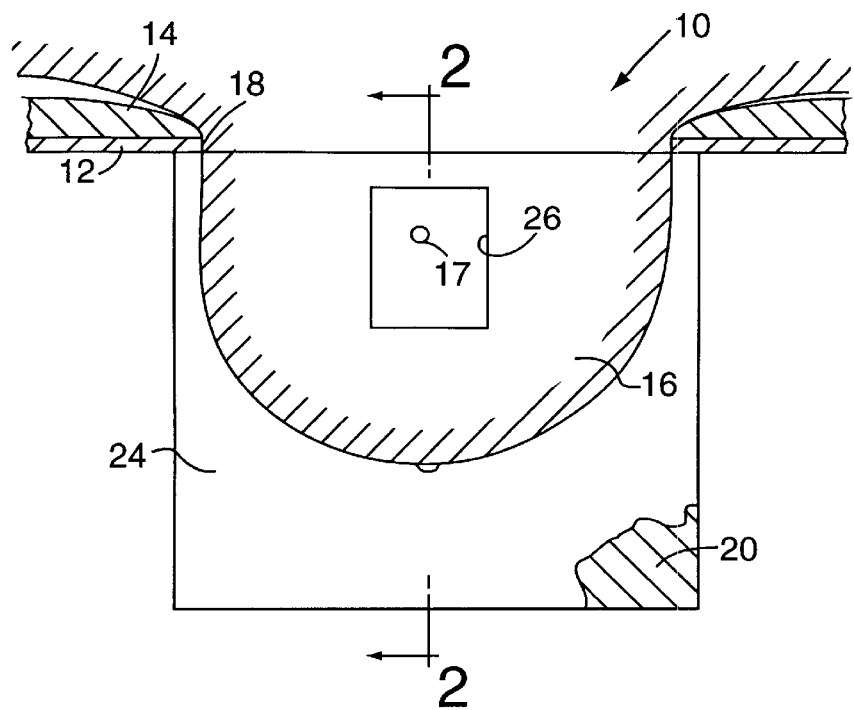
FIG. 1 is a front view of a prior art apparatus for performing stereotactic guided needle biopsy with a patient's breast shown disposed between a fixed plate and a pressure plate of the apparatus.
Figure 2:
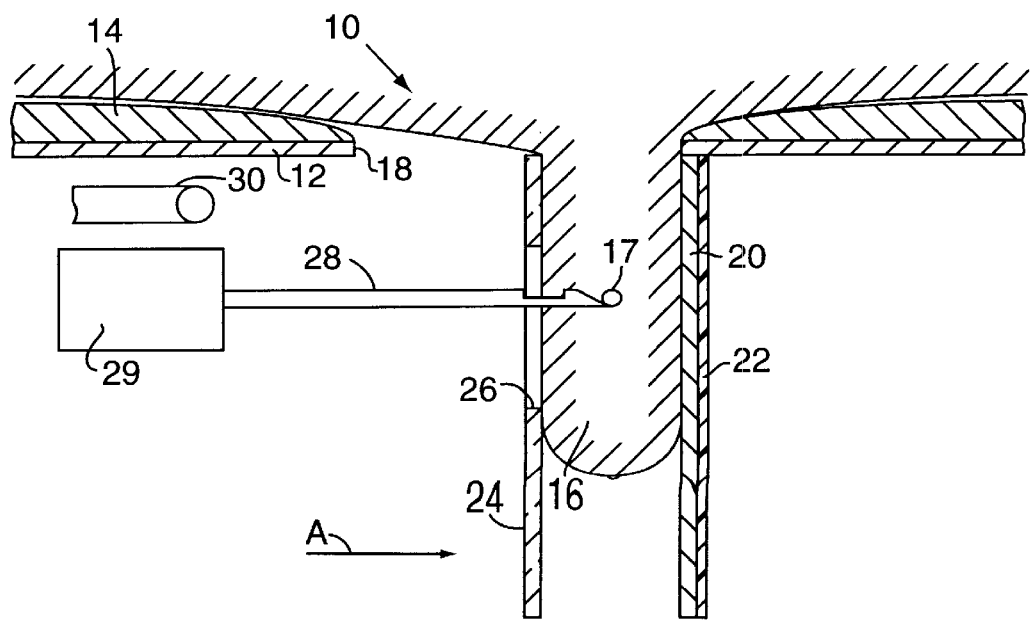
FIG. 2 is a cross section taken along the line 2—2 of the apparatus of FIG. 1 with the patient's breast shown pressed between fixed plate and the pressure plate of the apparatus.

Since, as noted above, breast tissue is not compressible, restriction of the inferior and lateral excursion of the breast by the bolster significantly reduces the radius of the breast and the surface area of the breast in contact with the plates as the bolster and the patient's breast are pressed between the plates. Accordingly, there is a corresponding increase in the thickness of the breast, as compared to the same breast pressed between the plates without the containing pressure applied by the bolster. The increase in breast thickness provided by the bolster is illustrated by comparing the thickness of the patient's breast as shown in FIG. 2 and the thickness of the breast as shown in FIG. 7.

The redistribution of breast tissue achieved with the use of the bolster provides sufficient breast thickness to permit injection of the needle 28 without the danger of the needle completely traversing the breast and impaling the patient's breast to the fixed plate 20. Thus, the present invention enables patients, who would otherwise have to undergo a surgical biopsy, to have breast lesions biopsied by the less invasive procedure of stereotactic needle biopsy. Moreover, since the compressible bolster provides additional support for the breast as the bolster and the patient's breast are pressed between the plates, the force necessary to secure the breast in position is reduced.

Accordingly, the patient experiences much less discomfort during the biopsy procedure, and the risk of tissue damage from prolonged and vigorous pressure which would otherwise have to be applied by the plates is significantly reduced. Still further, since the bolster assists in restricting the movement of the patient's breast between the plates, the risk of inadvertent and undetected repositioning of the breast during the needle biopsy procedure is reduced. This is critical, since such movement of the patient's breast could result in improper needle placement and incorrect tissue sampling.

As described above, a layer 68 of absorbent material is supported on the top surface 54 of the bolster. As shown best in FIG. 7, when the bolster 52 is placed against the patient's breast with the layer 68 of absorbent material immediately adjacent to the breast, the layer 68 extends vertically below the injection site 70 of the needle 28. Accordingly, any blood or other body fluids that exude from the injection site and seep between the pressure plate 24 and the patient's breast will flow by gravity into contact with the absorbent material. The material will contain and absorb these materials, thus preventing them from contaminating and potentially damaging the apparatus 10. Further, the layer of absorbent material reduces the exposure of operating personal to these body fluids.

While the support device of the present invention has been illustrated and described in connection with the preferred embodiment, it should be understood that the invention is not limited in this regard. For example, the bolster 52 is preferably a continuous strip of open cell polyurethane foam. However, other compressible materials, such as other open cell or partially open cell plastic foams, or synthetic or natural rubber are suitable for forming the bolseter. The important factors are that the material be sufficiently compressible so that it does not restrict movement of the plates while being sufficiently rigid to control the configuration of the patient's beast as the bolster and the patient's breast are pressed between the plates. In addition, the material must be sufficiently pliable to permit the bolster to conform to the changing configuration of the patient's breast as it is pressed between the plates, as well as conform to those portions of the biopsy apparatus which are in contact with the bolster.

Further, the support device of the present invention is not limited to the bolster 52 described and illustrated as the preferred embodiment. For example, instead of being provided as a continuous strip of foam, a plurality of discrete foam segments spaced between the plates and adjacent to the patients breast are also suitable. As the foam segments and the patient's breast are pressed between the plates, the foam segments are individually positioned adjacent a corresponding peripheral portion of the patient's breast until the breast is brought into the configuration illustrated in FIG. 7. Of course, each one of the foam segments can be individually provided with a layer of absorbent material supported on the surface of the segment disposed adjacent to the patient's breast.

It should also be understood that while the preferred embodiment of the invention is disclosed in connection with a stereotactic guided needle biopsy apparatus of the type illustrated in FIGS. 1, 2, 6 and 7, the invention is also suitable for use in apparatus having a different construction. For example, apparatus adaptable to standard mammography machines are known wherein the breast to be biopsied is positioned on a horizontal base, and a moveable pressure plate is disposed above and parallel to the base. To perform the biopsy, the pressure plate is lowered onto the breast. In a further modification, the base and the pressure plate are rotable from the horizontal position.

Accordingly, while preferred embodiments have been shown and described, various modifications and substitutions may be made without departing from the spirit and scope of the invention. It is, therefore, to be understood that the present invention has been described by way of example and not by limitation.

What is claimed:

1. An apparatus for performing stereotactic guided needle biopsy comprising a first plate and a second plate moveable with respect to one another and a support device, said support device comprising a compressible support having an inner surface extending adjacent to a substantial portion of a peripheral surface of a patient's breast when the breast and the compressible support are disposed between the first and second plates, said compressible support restricting inferior and lateral excursion of the breast as the first and second plates are moved toward one another and the patient's breast and the compressible support are pressed between the plates.

2. The support device of claim 1, wherein the compressible support is resilient.

3. The support device of claim 1, wherein the support device further comprises a layer of absorbent material disposed between the inner surface of the compressible support and the peripheral surface of the patient's breast for containing and absorbing blood and other body fluids exuded from a biopsy needle puncture site.

4. The support device of claim 3, wherein the layer of absorbent material is affixed to the inner surface of the compressible support.

5. The support device of claim 4, wherein the layer of absorbent material is removably affixed to the inner surface of the compressible support.

6. The support device of claim 2, wherein the compressible support comprises a flexible foam strip.

7. The support device of claim 2, wherein the compressible support comprises a plurality of discrete flexible foam segments.

8. The support device of claim 6, wherein the foam strip comprises an open cell plastic foam.

9. The support device of claim 1, wherein the support device maintains the patient's breast at a thickness in the range of at least about 35 cm.

10. A method for controlling the thickness of a patient's breast during stereotactic guided needle biopsy, wherein the biopsy is performed with an apparatus having a fixed plate and a pressure plate movable with respect to one another, said method comprising the steps of:

positioning the patient's breast between the fixed plate and the pressure plate;

positioning a compressible support between the fixed plate and the pressure plate and adjacent to a substantial portion of a peripheral surface of the patient's breast;

pressing the patient's breast and the compressible support between the fixed plate and the pressure plate;

and restricting the inferior and lateral excursion of the breast with the support to control the thickness of the patient's breast as the breast and the compressible support are pressed between the plates.

11. The method of claim 10, wherein the compressible support is resilient.

12. The method of claim 10, wherein the support device further comprises a layer of absorbent material disposed between the inner surface of the compressible support and the peripheral surface of the patient's breast for containing and absorbing blood aid other body fluids exuded from a biopsy needle puncture site.

13. The method of claim 12, wherein tile layer of absorbent material is affixed to the inner surface of the compressible support.

14. The method of claim 13, wherein the layer of absorbent material is removably affixed to the inner surface of the compressible support.

15. The method of claim 11, wherein the compressible support comprises a flexible foam strip.

16. The method of claim 11, wherein the compressible support comprises a plurality of discrete foam segments.

17. The method of claim 15, wherein the foam strip comprises an open cell plastic foam.

18. The method of claim 10, wherein the thickness of the patient's breast is controlled to a thickness sufficient to permit injection of a needle without the needle completely traversing the breast as the breast and the compressible support are pressed between the plates.

19. The method of claim 10, wherein the thickness of the patient's breast is controlled to a thickness in the range of at least about 3.5 cm.

20. The method of claim 10, wherein the compressible support at least partially restricts repositioning of the patient's breast during stereotactic guided needle biopsy.

* * * * *